United States Patent [19]

Brock et al.

[11] 4,218,471
[45] Aug. 19, 1980

[54] PROCESS FOR THE TREATMENT OF HUMANS SUFFERING FROM UNDESIRED UROTOXIC SIDE EFFECTS CAUSED BY CYTOSTATICALLY ACTIVE ALKYLATING AGENTS

[75] Inventors: Norbert Brock; Jurij Stekar, both of Bielefeld, Fed. Rep. of Germany

[73] Assignee: Asta-Werke Aktiengesellschaft Chemische Fabrik, Bielefeld, Fed. Rep. of Germany

[21] Appl. No.: 9,625

[22] Filed: Feb. 6, 1979

[30] Foreign Application Priority Data

Feb. 17, 1978 [DE] Fed. Rep. of Germany ... 2806866[U]

[51] Int. Cl.² ......................................... A61K 31/185
[52] U.S. Cl. .................................................. 424/315
[58] Field of Search ....................................... 424/315

[56] References Cited

PUBLICATIONS

Chemical Abstracts, 72:27807s (1970).

*Primary Examiner*—Jerome D. Goldberg

*Attorney, Agent, or Firm*—Schwartz, Jeffery, Schwaab, Mack, Blumenthal & Koch

[57] ABSTRACT

The invention is related to a process for the treatment of humans suffering from undesired urotoxic side effects caused by cytostatically active alkylating agents administered to them against malign tumors, comprising administering a pharmacologically acceptable salt of a dithiodi-(alkane sulfonic acid) having the general formula

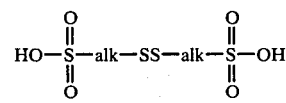

to the human treated with the cytostatically active alkylating agent, in an amount ranging from 20% of the weight of the alkylating agent to the highest tolerated dosage of the salt of the dithiodi-(alkane sulfonic acid), simultaneously or separately in combination with the alkylating agent.

7 Claims, No Drawings

PROCESS FOR THE TREATMENT OF HUMANS SUFFERING FROM UNDESIRED UROTOXIC SIDE EFFECTS CAUSED BY CYTOSTATICALLY ACTIVE ALKYLATING AGENTS

The present invention is directed to a new use of salts of dithiodi-(alkane sulfonic acids) in the cytostatic therapy with alkylating agents. More particularly, the present invention is related to a process for the treatment of humans who are treated with alkylating agents against malign tumors and who suffer from the undesired urotoxic side effects caused by such alkylating agents in the kidneys, urinary tracts and urinary bladder.

Cytostatically active alkylating agents such as melphalane, cyclophosphamide, trofosfamide, ifosfamide, sufosfamide, chlorambucil, busulfane, triethylene thiophosphamide or triaziquone and in particular the 2-oxo-1,3,2-oxazaphosphorinanes cyclophosphamide, trofosfamide, ifosfamide and sufosfamide produce undesired side effects such as serious irritations of the kidneys, the urinary tracts and/or the urinary bladder of the patient treated therewith. As is well known, such undesired side effects occur readily in particular after such organs have been damaged for the first time. The undesired side effects are sometimes produced to such a degree that the cytostatic therapy of the patient suffering from cancer has to be interrupted temporarily or is rendered even impossible at all. In view of the fact that malign tumors readily produce resistency against a particular cytostatic, such cytostatics are successful in the so-called high dosage therapy. In such a treatment, the cytostatic is administered at first in a dosage which is very high in comparison to the toxicity of the cytostatic in order to produce an initial dosage as high as possible of the cytostatic at the tumor tissue. Thereafter, the cytostatics are administered in several lower dosages over a prolonged period of time. It is known that such undesired side effects are caused by metabolites of the cytostatics produced in the body of the patient treated therewith. These undesired side effects quite often occur also with alkylating agents such as 2-[N,N-bis-(2-chloroethyl)-amino]-2-oxo-1,3,2-oxazaphosphorinane known under the well-known trade names Endoxan ® or Cytoxan ® or under the generic name cyclophosphamide, and 2-[N,N-bis-(2-chloroethyl)-amino]-3-(2-chloroethyl)-2-oxo-1,3,2-oxazaphosphorinane known under the trade name Ixoten ® or the generic name trofosfamide. Of even more importance are these undesired side effects when using alkylating agents having a high cytostatic activity at a lower toxicity such as 2-(N-2-chloroethyl-amino)-3-(2-chloroethyl)-2-oxo-1,3,2-oxazaphosphorinane known under the generic name ifosfamide. The therapeutic usefulness of such valuable alkylating agents which is particularly based upon the low toxicity, is again substantially limited by these undesired side effects. It has been observed recently that such irritations of the urinary bladder may even cause the formation of malign tumors there. Many experiments have been made in order to avoid or at least alleviate these detrimental and undesired side effects of the cytostatically active alkylating agents since they can no more be replaced in the treatment of malign tumors, and a premature rupture of the therapy would produce severe damage or premature death of the patient. One of the attempts consists in the administration of increased amounts of liquid, possibly in combination with the administration of agents increasing the formation of urine in order to obtain a passage of urine containing metabolites of cytostatics as quick as possible through the kidneys, the urinary tracts and the urinary bladder and to avoid the formation of high concentrations of metabolites in particular in the urinary bladder. This so-called hydratation in general is combined with an alkalinazation of the urine, for instance by means of the hexapotassium hexasodium pentacitrate hydrate complex known under the registered trade name Uralyt-U, and in particular by introducing solutions of mercapto group containing compounds into the urinary bladder by means of a catheter. With such mercapto group containing compounds it was supposed that the mercapto group undergoes reaction with the alkylating agent, thus inactivating the same. N-Acetyl cysteine and cysteine in particular have been used as such mercapto group containing compounds. However, the results only where very limited, in particular in cases where the cytostatics had to be administered in very high dosages. Furthermore, the washing of the urinary bladder or vesicoclysis is a procedure very burdensome to the patient, and can only very hardly be practiced in the treatment with cytostatics over prolonged periods of time. Furthermore, more upward areas in the urinary tracts cannot be reached by vesicoclysis.

The use of mercapto group containing compounds for the general detoxification in the therapy with alkylating agents has been first published by T. A. Connors, Europ. J. Cancer 2, 393 to 395 (1966). However, these experiments showed no result because the mercapto group containing compounds there used at the same time decreased the cytostatic activity of the alkylating agents (see in particular loc. cit. p. 300 and 303, last but one sentence).

After introduction of the 2-oxo-1,3,2-oxazaphosphorinanes as alkylating agents and after observation of urotoxic side effects (hemorrhaginal cysto-pyelonephritis), the first attempts to avoid such undesired side effects where made by topically applying mercapto group containing compounds in the urinary bladder itself. This instillation of N-acetylcysteine up to now represented a standard prophylaxis against urotoxic side effects when administering cyclophosphamide and ifosfamide at very high dosages (see for instance Hoefer-Janker et al., Med. Welt 26, 972 (1975); Drings et al., Verh. Dtsch. Ges. inn. Med. 78, 166 (1972); Cohen et al., Cancer Chemother.rep., Part 1, 59, 751 (197); Creaven et al., Cancer Treatm. Rep. 60, 445 (1976); and Primack, J. Nat. Cancer Inst. 47, 223 (1971)). However, the installation of HS-group containing compounds into the urinary bladder did not solve the problem of a general detoxification. The beneficial effects of the applied mercapto group containing compound were limited to the urinary bladder. Furthermore, the application by means of a catheter was not regarded as most favorable. Finally, the clinical effectiveness of this burdensome prophylaxis by no means was satisfactory (see for instance, Falkson, Suid-Afrikaanse Kankerbulletin 15, 97, 1971).

In U.S. patent application Ser. No. 967,000 filed Dec. 6, 1978 it is described that the above mentioned undesired side effects of alkylating cytostatics upon the kidneys the urinary tracts and the urinary bladder of the patients treated therewith may be overcome by using together therewith a member of the long known group of pharmacologically acceptable salts of mercapto alkane sulfonic acids having the general formula

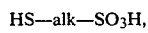

HS—alk—SO₃H, wherein alk is a straight or branched alkylene group having from 2 to 6, in particular from 2 to 4 carbon atoms in a particular relation to the application of the cytostatic, i.e. in an amount of at least 20% of the dosage of the cytostatic up to the highest tolerated dosage of the salt of the mercapto alkane sulfonic acid and, in particular within a period of about 30 minutes before administration of the cytostatic until about 30 minutes thereafter. However, the salts of mercapto alkane sulfonic acids quite often do not produce the desired protective activity because the course of excretion of the alkylating agents and of their alkylating metabolites is too different from the course of excretion of the protective agent. Furthermore, the salts of the mercapto alkane sulfonic acids are stable against oxidation by oxygen only to a limited extent which renders difficult in particular their conversion into pharmaceutical preparations to be administered perorally. This limited stability further causes a limited storage stability of such pharmaceutical preparations. However, the peroral administration showed to be of particular desirability because in view of the quicker excretion of the salts of the mercapto alkane sulfonic acid this protective agent has to be administered repeatedly during the treatment and because the intravenous application quite often is not possible since, as is well known, the blood vessels of the patients to be treated in most instances are in a very bad condition.

It surprisingly now has been found that the above described undesired urotoxic side effects produced by cytostatically active alkylating agents in the kidneys, the urinary tracts and the urinary bladder of patients treated therewith may be overcome in a simple manner and to a substantially complete degree by administering in combination with the alkylating agent a pharmacologically acceptable salt of a dithiodi-(alkane sulfonic acid) having the general formula

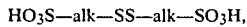

HO₃S—alk—SS—alk—SO₃H, wherein alk is a straight or branched alkylene group having from 2 to 6, in particular from 2 to 4 carbon atoms. The present invention therefore is directed to the use of such pharmacologically acceptable salts of dithiodi-(alkane sulfonic acids) in the catostatic therapy with alkylating agents, or, with other words, to a process for the treatment of humans treated with cytostatically active alkylating agents against malign tumors and suffering from the undesired urotoxic side effects caused by such alkylating agents in the kidneys, the urinary tracts and the urinary bladder. This process comprises administering such a pharmacologically acceptable salt of a dithiodi-(alkane sulfonic acid) during a period of from 120 minutes before administration of the alkylating agent until about 120 minutes after its administration and in an amount ranging from at least 20% of the amount of the alkylating agent administered or to be administered to the patient up to the highest dose of the dithiodi-(alkane sulfonic acid) which is tolerated by the patient. This result is most surprising because, up to now only compounds having a free mercapto group have been used in order to protect against the above described undesired side effects, and because it is known from similar compounds that the protective activity of mercapto compounds disappears when converting them into the corresponding disulfide. For instance, cysteine in comparison to the salts of the mercapto alkane sulfonic acids still has a limited but distinct protective activity against cytostatically active alkylating agents while the corresponding disulfide, i.e. cystine does not have any such protective activity. This corresponds to the known fact that organic disulfides cannot readily be reduced under in vivo conditions (see for instance Bertho and Grassman, Biochemisches Praktikum, 1936, p. 143 for the disulfide cysteine). It is furthermore known from other compounds with physiological activity which can be reduced that they are ineffective in the reduced form such is with ascorbinic acid over desoxyascorbinic acid.

The salt of the dithiodi-(alkane sulfonic acid) can be administered in the same usual form of administration as the cytostatic or in a form different therefrom. For instance, the cytostatic may be administered intravenously while the salt of the dithiodialkane sulfonic acid is administered perorally or intraperitoneally. Thus, the present invention is also directed to such forms of administration, i.e. pharmaceutical products containing a pharmacologically acceptable salt of the dithiodi-(alkane sulfonic acid) as sole active agent besides usual carrier materials or other additives or such pharmaceutical products containing this salt together with a cytostatically active alkylating agent and carrier materials and additives. The salts of the dithiodi-(alkane sulfonic acid) may be readily converted alone or together with the alkylating agent into all known forms of administration, in particular to pharmaceutical products to be administered perorally. It is preferred that the salt of the dithiodi-(alkane sulfonic acid) is administered simultaneously with the cytostatically active alkylating agent. This is particularly true with respect to the high initial dose as is usual in the high dosage therapy. In this case it is particularly preferred to administer both compounds in a single unit of administration.

Numerous compounds may be used as salt forming base as they are for instance known in connection with the mercapto alkane sulfonic acids (see U.S.-PS 2,694,732, German Offenlegungsschrift 1,629,629). Particularly useful are the alkali metal salts, in particular the sodium salts.

Particularly favorable results have been obtained, and therefore preferred among the salts of the dithiodi-(alkane sulfonic acids) are the salts of dithiodi-(ethane-β-sulfonic acid) or 2.2′-dithiodi-(ethane sulfonic acid) having the formula

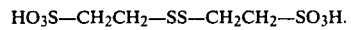

HO₃S—CH₂CH₂—SS—CH₂CH₂—SO₃H.

Most preferred among these salts is the disodium salt of dithiodi-(ethane-β-sulfonic acid). This is the most preferably used salt.

In order to obtain an effective protection of the patient to be treated with cytostatically active alkylating agents against the undesired urotoxic side effects upon the kidney, the urinary tracts and the urinary bladder it is sufficient to administer so small amounts as 20% of the amount of cytostatic. This is particularly true at low doses of the cytostatic. If the alkylating agent is to be administered in higher doses, the urotoxic side effect may be avoided with at least about 30% of the amount of the alkylating agent. Since the urotoxic side effects in particular occur upon administration of the cytostatic at high doses, the lower limit of 30% of the amount of cytostatic is the preferred lower limit for the amount of the salt of the dithiodi-(alkane sulfonic acid) administered for detoxification of the cytostatically active alkylating agent. In view of the very low toxicity of the pharmacologically acceptable salts of the dithiodi-(alkane sulfonic acids), the upper limit of the amount of salts of the dithiodi-(alkane sulfonic acids) is of minor importance. It is surprising and important that the cytostatic activity of the alkylating agent is not at all decreased or otherwise affected by the use of the salts of the dithiodi-(alkane sulfonic acids) in accordance with the present invention. Since the undesired urotoxic side effects even at high doses of the cytostatic may be substantially completely removed with equal amounts of salts of the dithiodi-(alkane sulfonic acids), it is preferred to use the salt of the dithiodi-(alkane sulfonic acid) in amounts corresponding to 30 to 150% of the amount of cytostatic.

While the salts of the dithiodi-(alkane sulfonic acids) may be used in combination with all of the cytostatically active alkylating agents to overcome the above described undesired urotoxic side effects these salts of the dithiodialkane sulfonic acids are of particular importance in combination with the 2-oxo-1,3,2-oxazaphosphorinanes cyclophosphamide, ifosfamide, trofosfamide and sufosfamide used to a great extent in the treatment of humans suffering from many kinds of cancer deceases.

The pharmacologically acceptable salts of dithiodi-(alkane sulfonic acids) used in accordance with the present invention are partially known compounds (see J.Org.Chem. 26 (1961) p. 1330). These salts up to now have however never been used for therapeutic purposes. Furthermore, these or similar disulfide compounds up to now never have been used to remove the described undesired urotoxic side effects of cytostatically active alkylating agents. Up to now the medical profession was of the opinion that the alkylating agents or, respectively, the metabolites thereof causing these undesired side effects have to be detoxified topically at the place where they produce the injury and damage and that mercapto group containing compounds have to be applied to these damaged areas (for instance by instillation into the urinary bladder of the cytostatically treated patients) so that they produce their beneficial detoxifying activity at the place of damage. Furthermore, it was the opinion of the medical profession that the cytostatic activity of the alkylating agents is produced just by the metabolites blamed for the urotoxic side effects and, on the other hand, it is the mercapto groups of the used compounds which produce the protective activity and that, therefore, the mercapto group containing compounds have to be administered as late as possible in the passage through the human body in order to avoid a negative influence upon the cytostatic activity of the alkylating agents and their metabolites. However, even with the mercapto group containing compounds used up to now the degree of detoxification only was quite limited. The undesired side effects described hereinabove can be overcome only to a very limited degree. With corresponding disulfides there was observed no protective activity at all. Thus, it is not only surprising that the salts of the dithiodi-(alkane sulfonic acids) used in accordance with the present invention produce a protective activity as such and to such an extent that the described undesired side effects are avoided substantially completely, but it is furthermore surprising that the salts of the dithiodi(alkane sulfonic acids) produce the full protective activity even upon oral administration.

The following examples serve to further illustrate the present invention without however limiting the same thereto.

EXAMPLE 1

In accordance with the known practice of therapy a patient 27 years old and suffering from a theratoid carcinoma of the testicle, at first is subjected to irradiation and thereafter is treated with ifosfamide [i.e. 2-(N-2-chloroethyl-amino)-3-(2-chloroethyl)-2-oxo-1,3,2-oxazaphosphorinane] at 5 times per day, each time with 60 mg./kg. intravenously and at 5 subsequent days. The patient is simultaneously hydrated by administration of 4 liters of water spread over the day and is alkalinized by administration of hexapotassium hexasodium pentacitrate hydrate complex. Despite this prophylatic treatment, the patient showed macrohematuria already on the fourth day. This necessitated immediate rupture of the therapy. After a recovery period of 14 days, the therapy is repeated. However, 60 mg/kg. of the disodium salt of 2,2'-dithiodi-(ethane sulfonic acid) is administered intravenously and simultaneously with each dose of 60 mg/kg. of ifosfamide. The patient is controlled daily for micro- and microhematuria and for albuminuria. At no time during the treatment erythrocytes, albumina or granular cylindrical cells were found in the urine of the patient.

EXAMPLE 2

In another patient suffering from the same tumor, the therapy at first is started with the oral administration of 60 mg./kg. of the disodium salt of 2.2'-dithiodi-(ethane sulfonic acid). Two hours thereafter, 60 mg./kg. of ifosfamide are administered intravenously. The same treatment, i.e. the combination of an oral preadministration of the disodium salt of 2,2'-dithiodi-(ethane sulfonic acid) and a subsequent intravenous administration of 60 mg./kg. of ifosfamide is repeated at 5 subsequent days. There was found no indication of any damage to the kidney or the urinary bladder or of hematuria or of albumina or granular cylindrical cells in the urine of the patient at any time during the treatment. In both the above treatments a moderate hydration (2 liters per day) has been carried out. The treatment rendered superfluous alkalinization as well as the most burdensome instillation of mercapto group containing compounds into the bladder of the patient by means of a catheter.

EXAMPLE 3

Another patient in a similar situation showed sensibilization for a damage of the urinary bladder upon a preceeding regional radiotherapy. According to the general experience with such patients, there occurs very readily hemorrhoidal cystitis despite application of all known prophylactic treatments such as hydration, alkalinization or instillation of mercapto group containing compounds into the urinary bladder. However, even with this pretreated patient there did not occur any damage to the kidneys and the urinary bladder upon ifosfamide therapy (60 mg./kg. of intravenous single dose over 5 days) and simultaneous intravenous administration of 60 mg./kg. of the disodium salt of 2.2'-dithiodi-(ethane sulfonic acid).

EXAMPLE 4

In accordance with the known practice of therapy, a female patient 48 years old and suffering from a cancer of the ovary, at first is subjected to irradiation and thereafter is treated with ifosfamide [i.e. 2-(N-2-chloroethyl-amino)-3-(2-chloroethyl)-2-oxo-1,3,2-oxazaphosphorinane] at 5 times per day, each time with 60 mg./kg. intravenously and at 5 subsequent days. Despite hydration and alkalinization of the urine the patient showed microhematuria which necessitated the rupture of the treatment. After a recovery period of 14 days the therapy is repeated. However, 35 mg./kg. of the sodium salt of 2-mercapto ethane sulfonic acid is administered intravenously and simultaneously with each dose of 60 mg./kg. of ifosfamide, 60, 120 and, respectively, 180 minutes after this intravenous injection 45 mg. of the disodium salt of 2,2'-dithiodi-(ethane sulfonic acid) each time are administered to the patient. The patient is controlled daily for micro- and macrohematuria and for albuminuria. There was found no indication of hematuria or albuminuria. The examination of the urine upon cytotoxic activity at varying times after administration of ifosfamide also was negative. No cytostatically active metabolites were found in the urine.

The same protective treatment was effected with the same favourable results in patients suffering from other cancer deceases such as parvicellular bronchial carcinoma or pancreatic carcinoma.

EXAMPLE 5

One part by weight of ifosfamide [i.e. 2-(N-2-chloroethyl-amino)-3-(2-chloroethyl)-2-oxo-1,3,2-oxazaphosphorinane] and one part by weight of the disodium salt of 2.2'-dithiodi-(ethane sulfonic acid), both in pure sterile form, are homogenously mixed under sterile conditions in a sterile mixer and filled into injection ampoules such that each ampoule contains 500 mg. of ifosfamide and 500 mg. of the disodium salt of 2,2'-dithiodi-(ethane sulfonic acid) per 10 ml. of injection solution.

EXAMPLE 6

Jacketed tablets each weighing 600 mg. are produced, each unjacketed tablet weighing 200 mg. and containing 50 mg. of trofosfamide [i.e. 2-(N,N-di-2-chloroethyl-amino)-3-(2-chloroethyl-amino)-3-(2-chloroethyl)-2-oxo-1,3,2-oxazaphosphorinane] and 50 mg. of the disodium salt of 2.2'-dithiodi-(ethane sulfonic acid) as active ingredients and 62.3 mg. of corn starch, 17.8 mg. of lactose, 0.9 mg. of gelatine, 12.0, g. of talcum, 4.0 mg. of magnesium stearate and 3.0 mg. of aerosil as carried materials and additives. The jacket weighing 400 mg. for each tablet contains 154.0 mg. of corn starch, 115.0 mg. of lactose, 106.5 mg. of calcium phosphate, 5.7 mg. of gelatein, 2.8 mg. of glycerine, 12.0 mg. of talcum and 4.0 mg. of magnesium stearate.

0.4 kg. of corn starch and 0.178 kg. of lactose are thoroughly mixed with 0.18 kg. of a 5% aqueous gelatine solution and the mixture is granulated through a 2 mm. sieve and the granulated material is dried. The granulated material together with 0.5 kg. of trofosfamide, 0.5 kg. of the disodium salt of 2.2'-dithiodi-(ethane sulfonic acid), 0.223 kg. of corn starch, 0.120 kg. of talcum, 0.030 kg. of aerosil and 0.040 kg. of magnesium stearate are passed through a 1 mm. sieve. This material is homogenously mixed and pressed in a concentrically running press to kernels haaving a diameter of 9 mm., a curvature radius of 7.5 mm. and each weighing 200 mg.

A 5% aqueous gelatine solution is prepared from 0.057 kg. of gelatine and 0.028 kg. of glycerine and water. A homogenous mixture of 1.540 kg. of corn starch, 1.150 kg. of lactose and 1.065 kg. of calcium phosphate is humidified and thoroughly mixed with the gelatine solution. The mixture thereafter is granulated through a 2 mm. sieve and the granulated material is dried. The granulated product finally is passed through a 1 mm. sieve together with 0.120 kg. of talcum and 0.040 kg. of magnesium stearate and is homogenously mixed thus producing the jacketing granulate ready for pressing.

The above obtained kernels and this jacketing granulate are converted to jacketed tablets in a Kilian Prescoter machine to obtaine jacketed tablets each weighing 600 mg. and having a diameter of 12 mm. and a curvature radius of 12.5 mm.

EXAMPLE 7

20.0 kg. of the disodium salt of 2,2'-dithiodi-(ethane sulfonic acid) are dissolved in water for injection purposes to yield a solution of 100.0 liters. This 20% aqueous solution is clear and colourless and is filled into 5 ml. ampoules such that each ampoule contains 1 g. of active material. After sterilization in a usual manner the ampoules are ready for use.

EXAMPLE 8

7.500 kg. of the disodium salt of 2,2'-dithiodi-(ethane sulfonic acid), 0.900 kg. of lactose, 0.900 kg. of calcium phosphate and 1.200 kg. of corn starch are thoroughly mixed, humidified with 1.5 l. of a 5% gelatine solution containing 0.075 kg. of gelatine and the mixture is passed through a 2 mm. sieve. The resulting granulate is dried and passed through a 1 mm. sieve together with 0.375 kg. of Plasdone XL, 0.225 kg. of talcum and 0.075 kg. of magnesium stearate and is homogenously mixed. The resulting mixture is pressed to kernels each weighing 700 mg. and having a diameter of 13 mm. and a curvature radius of 18 mm.

170.0 g. of lactose, 17.0 g. of polyglycol 6000 and 17.0 g. of Tween 20 are dissolved in 1021.7 g. of purified water. 176.8 g. of titanium dioxide TiO$_2$ and 170.0 g of talcum are suspended in the solution. Thereafter, 127.5 g. of Eudragit E 30 d are added to the suspension with stirring and the suspension is coated upon the kernels such that each kernel is covered by a jacket weighing 24.0 mg.

What we claim is:

1. Process for the treatment of humans suffering from the undesired urotoxic side effects caused by cytostatically active alkylating agents selected from the group consisting of melphalane, cyclophosphamide, trofosfamide, ifosfamide, sufosfamide, chlorambucil, busulfane, triethylene thiophosphamide or triaziquone in the kidneys, urinary tracts and urinary bladder comprising administering a pharmacologically acceptable salt of a dithiodi-(alkane sulfonic acid) having the general formula

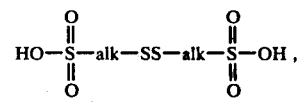

wherein alk is a member selected from the group consisting of the straight and branched alkylene groups having from 2 to 6 carbon atoms, to the human treated with the alkylating agent in an amount ranging from 20% to about 150% of the weight of the dose of the alkylating agent of the salt of the dithiodi-(alkane sulfonic acid).

2. Process as claimed in claim 1 wherein the salt of the dithiodi-(alkane sulfonic acid) is administered to the patient within the period ranging from about 30 minutes before the administration of the cytostatically active alkylating agent up to about 30 minutes after its administration.

3. Process as claimed in claim 1 wherein at least 25% of the total dose of the salt of the dithiodi-(alkane sulfonic acid) is administered in a period ranging from about 30 minutes before the administration of the cytostatically active alkylating agent until about 30 minutes after its administration while the remainder of the total dose is administered to the human in a single or in several separate partial doses within a period of up to 12 hours after the administration of the cytostatically active alkylating agent.

4. Process as claimed in claim 1 wherein the salt of the dithiodi-(alkane sulfonic acid) is administered to the human in an amount ranging from 30 to 100% of the weight of the dose of the cytostatically active alkylating agent.

5. Process as claimed in claim 1 wherein alk is the 1,2-ethylene group.

6. Process as claimed in claim 5 wherein the pharmacologically acceptable salt of the dithiodi-(alkane sulfonic acid) is an alkali metal salt.

7. Process as claimed in claim 6 wherein the pharmacologically acceptable salt is the di-sodium salt.

* * * * *